United States Patent [19]

Yoshikawa et al.

[11] Patent Number: 4,691,037
[45] Date of Patent: Sep. 1, 1987

[54] RUTHENIUM-PHOSPHINE COMPLEX

[75] Inventors: Sadao Yoshikawa; Masahiko Saburi; Takao Ikariya; Youichi Ishii, all of Tokyo; Susumu Akutagawa, Kanagawa, all of Japan

[73] Assignee: Takasago Perfumery Co., Ltd., Tokyo, Japan

[21] Appl. No.: 816,689

[22] Filed: Jan. 6, 1986

Related U.S. Application Data

[63] Continuation-in-part of Ser. No. 709,869, Mar. 8, 1985, abandoned.

[30] Foreign Application Priority Data

Sep. 4, 1984 [JP] Japan .................. 59-183875

[51] Int. Cl.⁴ ......................................... C07F 15/00
[52] U.S. Cl. .................................. 556/18; 544/64; 546/2; 546/9; 546/11; 548/101; 556/23
[58] Field of Search ............. 556/18, 23; 544/64; 546/2, 9, 11; 548/101

[56] References Cited

U.S. PATENT DOCUMENTS 3,644,446  2/1972  Booth et al.
3,878,122  4/1975  Pennalla
4,268,454  5/1981  Pez et al.

*Primary Examiner*—Helen M. S. Sneed
*Attorney, Agent, or Firm*—Sughrue, Mion, Zinn, Macpeak, and Seas

[57] ABSTRACT

A ruthenium-phosphine complex represented by the formula (I)

$$Ru_xH_yCl_z(R\text{—}BINAP)_2(S)_p \quad (I)$$

wherein R—BINAP represents tertiary phosphine represented by the formula (II)

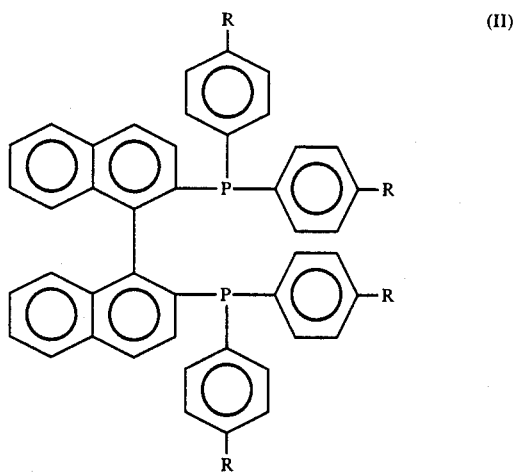

R which is the same represents hydrogen, methyl or t-butyl, S represents tertiary amine, y represents 0 or 1, and when y is 0, x represents 2, z represents 4 and p represents 1, and when y is 1, x represents 1, z represents 1 and p represents 0.

1 Claim, 4 Drawing Figures

FIG. 2  Ru₂Cl₄(p-Tolyl-BINAP)₂Et₃N

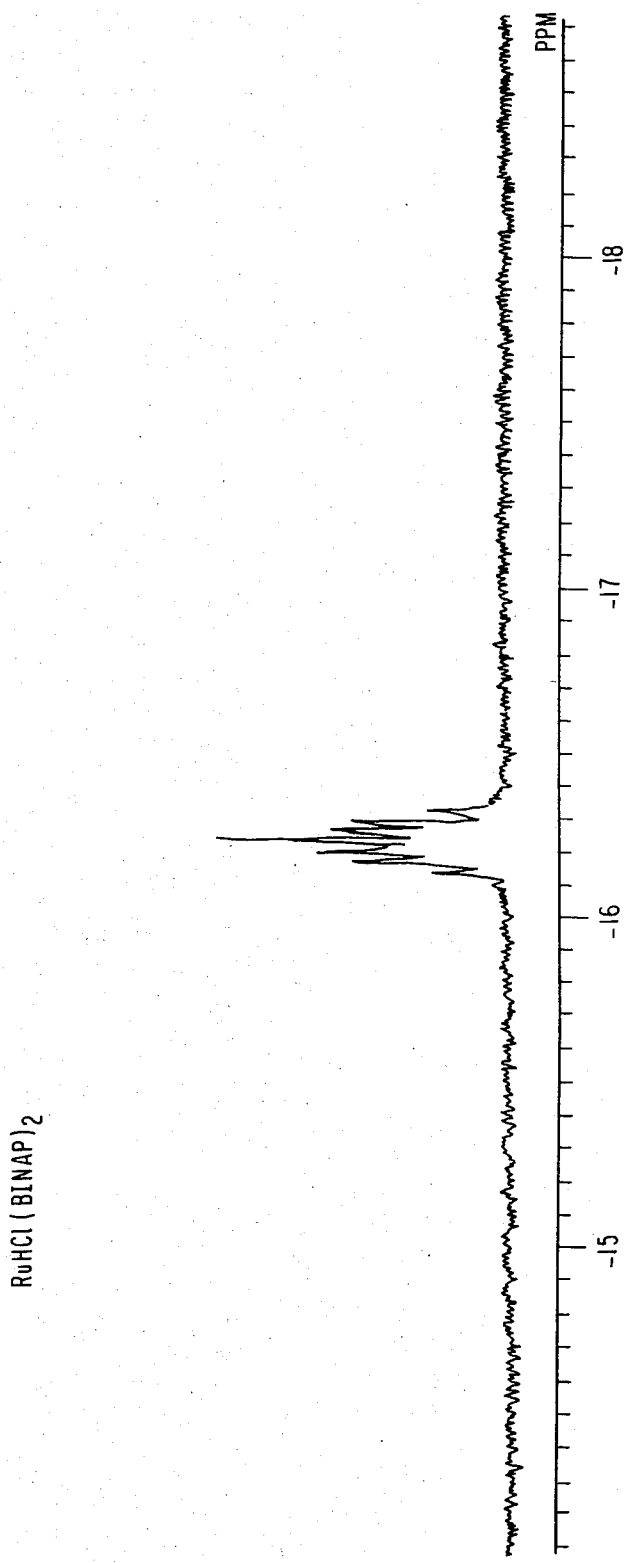
FIG. 4   RuHCl(BINAP)₂

RUTHENIUM-PHOSPHINE COMPLEX

CROSS-REFERENCE TO THE RELATED APPLICATION

This application is a continuation-in-part application of U.S. patent application Ser. No. 709,869, filed on Mar. 8, 1985 entitled RUTHENIUM-PHOSPHINE COMPLEX, now abandoned.

FIELD OF THE INVENTION

The present invention relates to a ruthenium-phosphine complex. More particularly, it is concerned with a ruthenium-phosphine complex which is used as an industrial catalyst in various organic syntheses and asymmetric syntheses such as an asymmetric hydrogenation reaction, an asymmetric reduction reaction and an asymmetric dehydrogenation reaction.

BACKGROUND OF THE INVENTION

Various organic synthesis reactions using a metal complex as a catalyst have been developed and utilized for many purposes. In particular, extensive investigations on the asymmetric synthesis have recently been made and the asymmetric synthesis is utilized to synthesize physiologically active substances and also natural products.

Of metal complexes such as nickel, palladium and rhodium, a metal complex of rhodium metal and an optically active tert-phosphine is particularly known as a catalyst for asymmetric hydrogenation catalyst. For example, a rhodium-phosphine complex having 2,2'-bis(diphenylphosphino)-1,1'-binaphthyl (hereinafter referred to as "BINAP" for simplicity) as a ligand is described, for example, in Japanese Patent Application (OPI) No. 61937/80 (the term "OPI" as used herein refers to a "published unexamined Japanese patent application").

The present inventors have previously reported the formation of a optically active lactone by an asymmetric hydrogenation reaction and asymmetric dehydrogenation of prochiral or meso-type cyclic acid anhydride or diol using a ruthenium complex catalyst having DIOP (2,3-o-isopropylidene-2,3-dihydroxy-1,4-bis(diphenylphosphino)butane) as a ligand in S. Yoshikawa et al, *TETRAHEDRON LETTERS*, Vol. 22 (1981) 4297-4300 and *CHEMISTRY LETTERS*, (1982) 1179-1182. Those reactions are classified into enantiotopic differentiating reaction wherein one of enantiotopic functional groups of substrate is selectively converted, and is an interesting reaction as a catalyst reaction.

Rhodium metal is an excellent metal for complex catalyst, but the place and amount of production thereof are limited and the rhodium is expensive. Therefore, in the case of using rhodium as a catalyst, the proportion of the rhodium cost in the product cost increases and this effects the production cost of goods. Ruthenium metal is inexpensive as compared with rhodium and is expected as an industrially advantageous catalyst. However, an asymmetric ruthenium complex merely includes a few examples other than a complex of DIOP such as $Ru_2Cl_4(DIOP)_3$ and has the problems on the precision and utilization of reaction. Therefore, development of a ruthenium complex catalyst which is useful to reduce the cost of product is demanded.

SUMMARY OF THE INVENTION

As a result of extensive investigations to meet the industrial demands, the present inventors have found a novel ruthenium-phosphine complex catalyst which can be used as a general organic synthesis catalyst by using ligands having no optical activity and which can be used as an asymmetric synthesis catalyst by using ligands having an optical activity, and established the synthesis method.

Accordingly, an object of the present invention is to provide a ruthenium-phosphine complex represented by the formula (I):

$$Ru_xH_yCl_z(R\text{—}BINAP)_2(S)_p \qquad (I)$$

wherein R—BINAP represents tertiary phosphine represented by the formula (II)

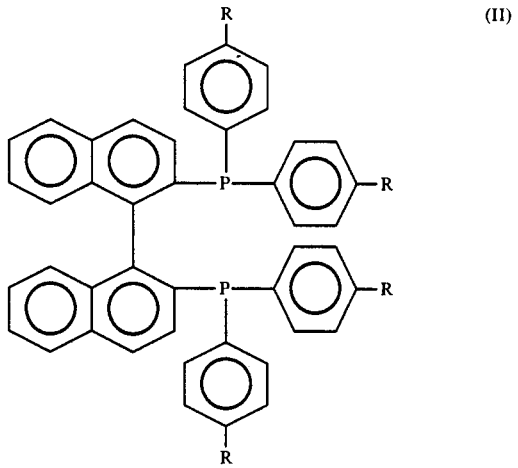

R which is the same represents hydrogen, methyl or t-butyl, S represents tertiary amine, y represents 0 or 1, and when y is 0, x represents 2, z represents 4 and p represents 1, and when y is 1, x represents 1, z represents 1 and p represents 0.

BRIEF DESCRIPTION OF THE DRAWINGS

FIGS. 3 and 4 each is a proton NMR spectrum obtained in Example 4 of the present invention.

DETAILED DESCRIPTION OF THE INVENTION

Figure 1:
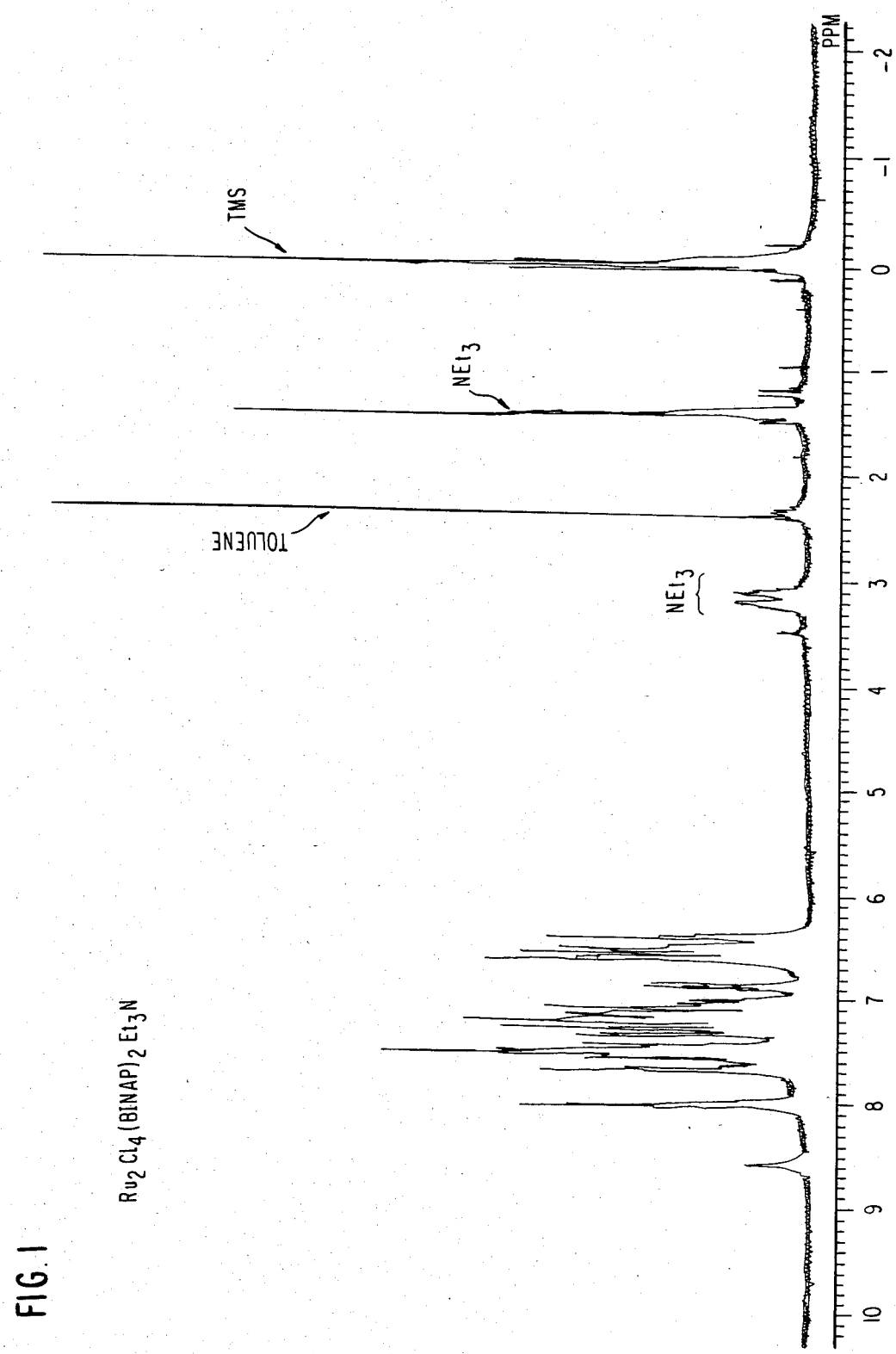
FIG. 1 is a proton NMR spectrum of the complex obtained in Example 1 of the present invention.

The novel ruthenium-phosphine complex according to the present invention can be easily prepared by reacting $[RuCl_2(COD)]_n$ wherein COD represents cyclooctadiene, with R—BINAP in the presence of a tertiary amine in a solvent.

Examples of the tertiary amine which can be used in the present invention include triethylamine, tri-n-butylamine, tri-n-octylamine, N-methyl piperidine, N-methyl pyrrolidine, N-methyl morpholine, pyridine, dimethyl aniline and tetramethyl ethylenediamine.

In particular, 1 mol of $[RuCl_2(COD)]_n$, 1.2 mols of R—BINAP and 4 mols of triethylamine are reacted in a solvent such as toluene under heating to obtain the desired complex in good yield. Further, 1 mol of

[RuCl$_2$(COD)]$_n$, 2 mols of R—BINAP and 4 mols of triethylamine are reacted in a solvent such as ethanol under heating to obtain the desired complex in good yield.

[RuCl$_2$(COD)]$_n$ which can be used in the present invention can be obtained by reacting ruthenium chloride with cycloocta-1,5-diene in an ethanol solution as disclosed in, for example, M. A. Bennett et al, *CHEMISTRY AND INDUSTRY* (1959) 1516.

R—BINAP includes a racemic form and an optically active form. The preparations thereof are exemplified as follows.

PREPARATION OF P-TOLYL BINAP

Bromine is reacted with 1,1'-binaphthol to prepare 2,2'-dibromo-1,1'-binaphthyl. The resulting product is subjected to the preparation method of the conventional Grignard reagent, e.g., using magnesium, to prepare Grignard reagent. The resulting reagent is condensed with di-p-tolylphosphinylchloride to obtain ($\pm$)-2,2'-bis(di-p-tolylphosphinyl)-1,1'-binaphthyl. The resulting product is heated together with trichlorosilane to reduce. thereby obtaining ($\pm$)-2,2'-bis(di-p-tolylphosphino)-1,1'-binaphthyl (hereinafter referred to a "p-Tolyl BINAP").

In the case of obtaining p-Tolyl BINAP which is an optically active form, the method disclosed in Henri Brunner, Angw. Chem. Int. Edt. Engl. 18, 620 (1979) is employed. That is, ($\pm$)-2,2'-bis(di-p-tolylphosphinyl)-1,1'-binaphthyl is resolved using dibenzoyl tartrate to separate an optically active substance, and the resulting product is reduced with trichlorosilane to obtain optically active p-Tolyl BINAP (cf. Japanese Patent Application No. 53600/84).

PREPARATION OF BINAP

BINAP is obtained by reacting bromine and 1,1'-bis-2-naphthol using triphenylphosphine as a reaction aid to obtain 2,2'-dibromo-1,1'-binaphthyl and adding chlorodiphenylphosphine to the resulting product in the presence of t-butyl lithium to conduct reaction (cf. Japanese Patent Application (OPI) No. 61937/80).

In the case of obtaining BINAP which is an optically active form, BINAP is oxidized with peracetic acid or hydrogen peroxide to obtain the dioxide thereof (hereinafter referred to as "BINAPO"), and using a lower alkyl acetate as a solvent, an optical resolution agent is acted on the resulting dioxide in the solvent. An optically active camphor-10-sulfonic acid or 3-bromocamphor-10-sulfonic acid is used as the optical resolution agent. The diastereoisomer salt crystallized is isolated and hydrolyzed to obtain an optically active BINAPO. The resulting BINAPO is reacted with trichlorosilane or methyl polysiloxane to obtain an optically active BINAP (cf. Japanese Patent Application No. 30799/83).

The present invention is described in greater detail by reference to the following non-limiting Examples and Application Examples.

EXAMPLE 1

Ru$_2$Cl$_4$((−)BINAP)$_2$Et$_3$N 1 g (3.56 mmol) of [RuCl$_2$(COD)]$_n$, 2.66 g (4.27 mmol) of (−)-BINAP and 1.5 g of triethyl amine were added to 100 ml of toluene under nitrogen atmosphere. Toluene was refluxed with heating and stirring to conduct the reaction for 10 hours. After cooling the reaction mixture, the crystals precipitated were separated by filtration. The resulting crystals were dissolved in toluene and ether was gradually added thereto to conduct recrystallization, thereby obtaining 2.4 g of orange fine crystals. The yield was 80%.

The elemental analysis values of the complex thus obtained are as follows.

|  | C | H | N | Cl |
|---|---|---|---|---|
| Found | 67.6 | 4.79 | 0.79 | 9.41 |
| Calculated | 66.7 | 4.67 | 0.83 | 8.4 |

The resulting complex was tested according to the proton NMR spectroanalysis and the spectrum obtained is shown in FIG. 1.

EXAMPLE 2

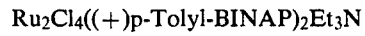
Ru$_2$Cl$_4$((+)p-Tolyl-BINAP)$_2$Et$_3$N

The procedure of Example 1 was repeated except for adding 1 g (3.56 mmol) of [RuCl$_2$(COD)]$_n$, 2.9 g (4.27 mmol) of (+)p-Tolyl-BINAP and 1.5 g of triethyl amine to 50 ml of toluene and refluxing under heating for 6 hours to obtain crystals, and after recrystallization, 2.24 g of purified crystals was obtained.

The elemental analysis values of the complex thus obtained are as follows.

|  | C | H | N | Cl |
|---|---|---|---|---|
| Found | 66.4 | 5.3 | 0.73 | 10.5 |
| Calculated | 67.9 | 5.3 | 0.78 | 7.9 |

Figure 2:
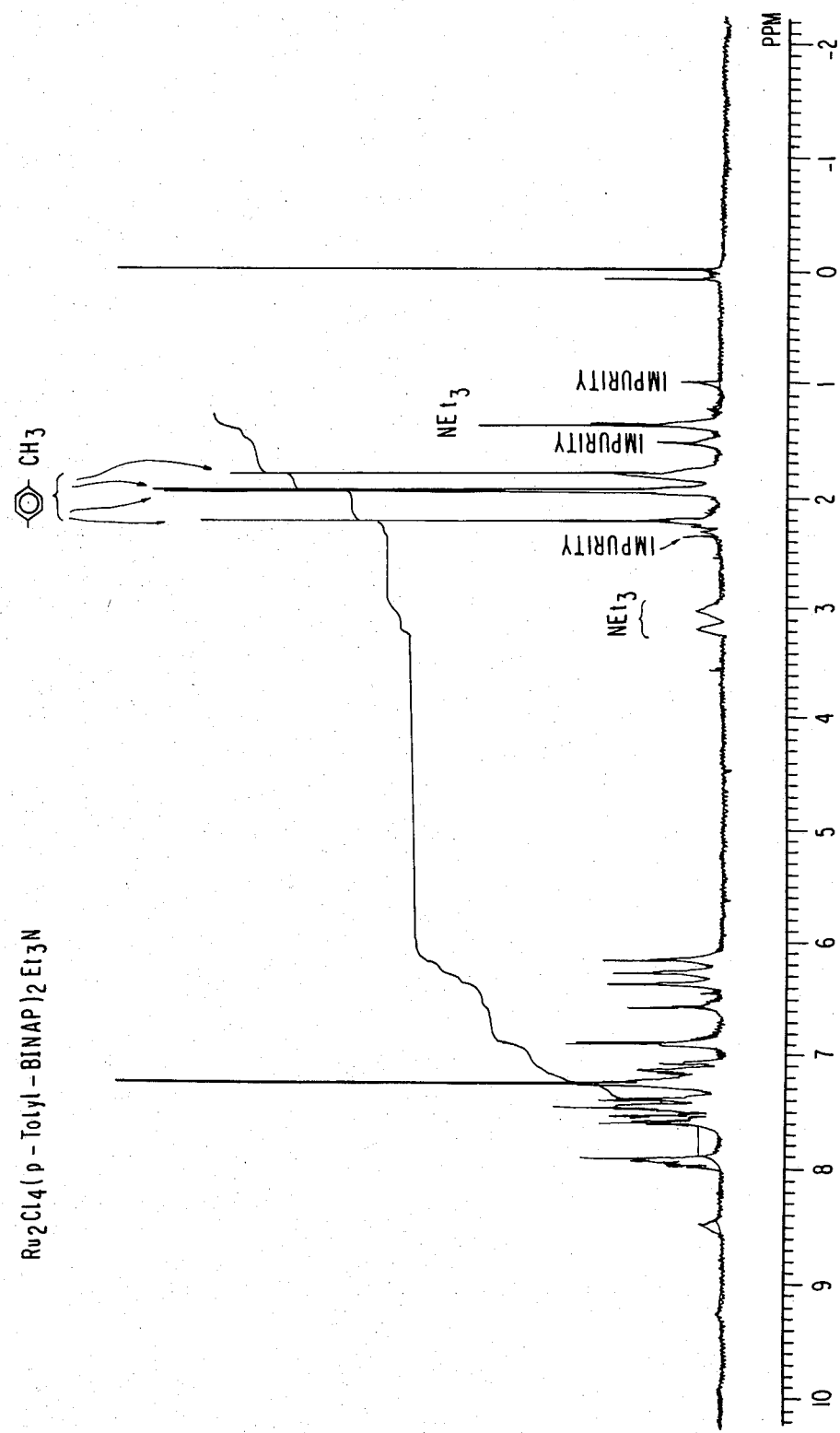
FIG. 2 is a proton NMR spectrum of the complex obtained in Example 2 of the present invention.

The resulting complex was tested according to the proton NMR spectroanalysis and the spectrum obtained is shown in FIG. 2.

EXAMPLE 3

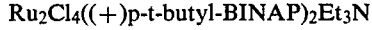
Ru$_2$Cl$_4$((+)p-t-butyl-BINAP)$_2$Et$_3$N

The procedure of Example 1 was repeated except for using 1 g (3.56 mmol) of [RuCl$_2$(COD)]$_n$, 3.64 g (4.3 mmol) of (+)p-t-butyl-BINAP and 1.5 g of triethyl amine to obtain crystals, and after recrystallization, 2.95 g of purified crystals was obtained.

The elemental analysis values of the complex thus obtained are as follows.

|  | C | H | N | Cl |
|---|---|---|---|---|
| Found | 70.86 | 6.31 | 0.76 | 7.04 |
| Calculated | 70.07 | 6.69 | 0.66 | 6.64 |

EXAMPLE 4

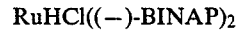
RuHCl((−)-BINAP)$_2$ 0.5 g (1.78 mmol) of [RuCl$_2$(COD)]$_n$, 2.5 g (4.0 mmol) of (−)-BINAP, 0.8 g (8 mmol) of triethyl amine and 50 ml of ethanol were introduced into a reactor and refluxed with heating for 6 hours under nitrogen atmosphere. After completion of the reaction, ethanol was distilled away, the residue was dissolved by adding 20 ml of dichloromethane and the insoluble portion was removed by filtration. Ether was gradually added to the filtrate to recrystallize. The crystals precipitated were separated by filtration and dried in vacuo to obtain 1.7 g of yellow crystals.

The elemental analysis values of the complex thus obtained are as follows.

|  | C | H | Cl |
|---|---|---|---|
| Found | 76.3 | 4.7 | 2.6 |
| Calculated | 76.9 | 4.6 | 3.0 |

Figure 3:
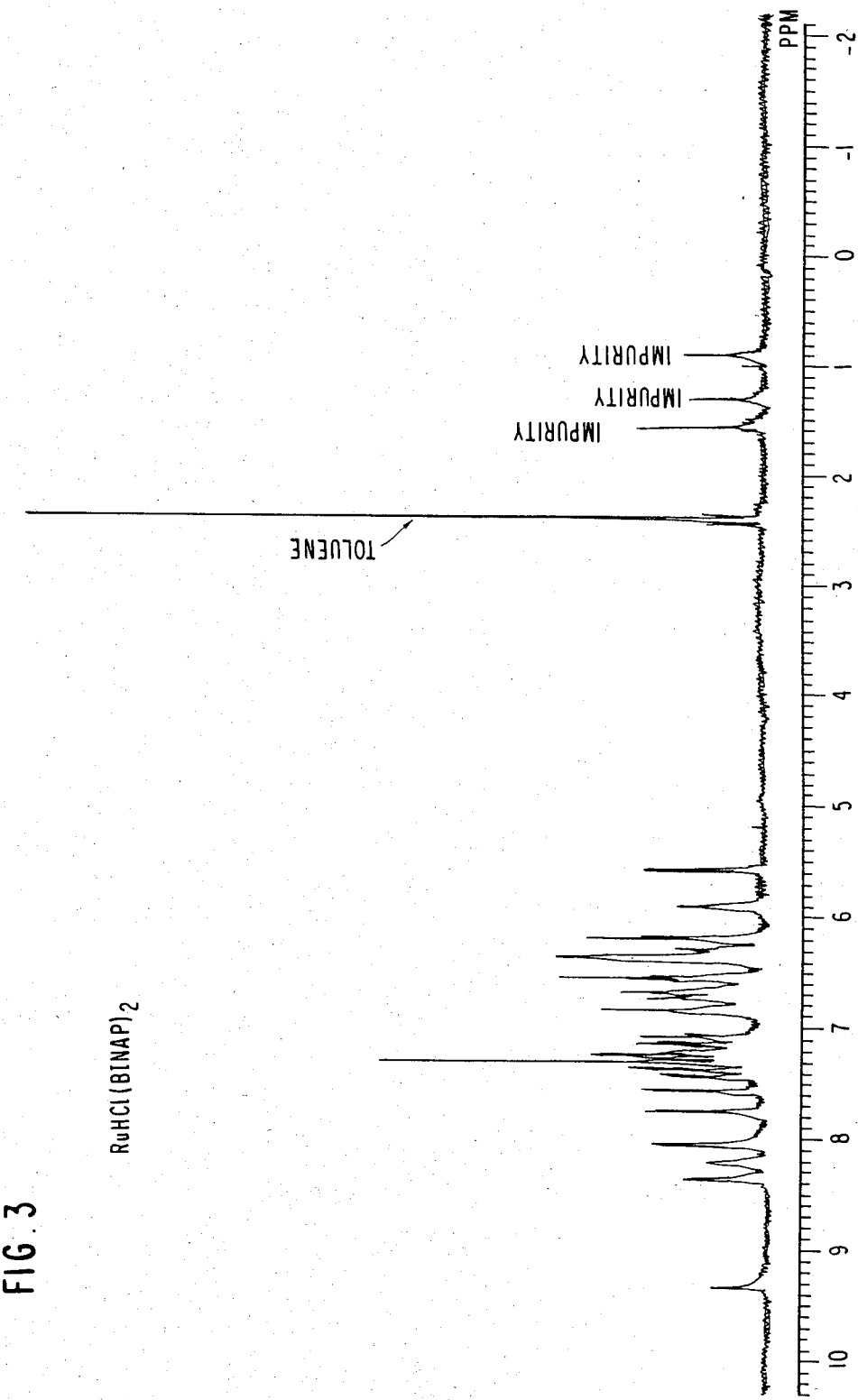

The resulting complex was tested according to the proton NMR spectroanalysis and the spectra obtained are shown in FIGS. 3 and 4.

EXAMPLE 5

RuHCl((−)-BINAP)$_2$ 2.4 g (2.8 mmol) of Ru$_2$Cl$_4$((−)-BINAP)$_2$Et$_3$N complex obtained in Example 1, 1.75 g (2.8 mmol) of (−)-BINAP and 1.2 g of triethyl amine were dispersed in 50 ml of toluene and the resulting mixture was sufficiently stirred for 20 hours under a hydrogen pressure of 1 atom. When the reaction was completed, yellow crystals precipitated. The crystals were separated by filtration and dried in vacuo to obtain 2.71 g of crystals. The crystals thus obtained were the same as the complex obtained in Example 4.

EXAMPLE 6

Ru$_2$Cl$_4$((+)-BINAP)$_2$Bu$_3$N 1 g (3.56 mmol) of [RuCl$_2$(COD)]$_n$, 2.66 g (4.27 mmol) of (+)-BINAP and 2.7 g of tri-n-butylamine were added to 100 ml of toluene. Atmosphere of the system was sufficiently replaced by nitrogen and the mixture was refluxed for 15 hours. After completion of the reaction, toluene and excess tri-n-butylamine were distilled away, and dichloromethane which had been degased, dried and purified was added to the resulting residue to form a uniform solution. When diethyl ether which had been degased, dried and purified was gradually added to the resulting solution, crystals began to precipitate. When the crystal began to precipitate, addition of diethyl ether was stopped, and the resulting mixture was allowed to stand at 0° to −10° C. for 24 hours. The crystals precipitated were separated by filtration, washed with ether sufficiently and dried at room temperature under a reduced pressure of about 1 mmHg for about 5 hours to obtain 2.05 g of crystals (Theoretical yield: 65%).

The elemental analysis values of the complex thus obtained are as follows.

|  | C | H | N | Cl |
|---|---|---|---|---|
| Found | 67.8 | 5.45 | 0.68 | 7.85 |
| Calculated | 67.67 | 5.13 | 0.79 | 8.00 |

EXAMPLE 7

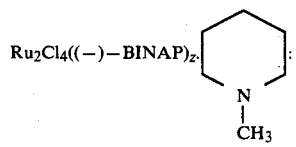

1 g (3.56 mmol) of [RuCl$_2$(COD)]$_n$, 2.66 g (4.27 mmol) of (−)-BINAP and 1.5 g of N-methyl piperidine were added to 100 ml of toluene, and the resulting mixture was refluxed for 15 hours under nitrogen atmosphere. After completion of the reaction, toluene and excess N-methyl piperidine were distilled away and the resulting residue was dissolved in dichloromethane of the minimum amount which can form a uniform solution. The insoluble residue was removed by filtration and ether was gradually added to the filtrate to precipitate crystals. The resulting mixture was allowed to stand in a refrigerator overnight The crystals were separated by filtration and dried at 25°–30° C. under a reduced pressure of about 1 mmHg for about 1 hour to obtain 1.74 g of crystals (Theoretical yield: 58%).

The elemental analysis values of the complex thus obtained are as follows.

|  | C | H | N | Cl |
|---|---|---|---|---|
| Found | 67.1 | 4.82 | 0.79 | 8.03 |
| Calculated | 66.86 | 4.56 | 0.83 | 8.42 |

APPLICATION EXAMPLE 1

0.1 g of the complex obtained in Example 1, 1 g of benzamidocinnamic acid, 0.4 ml of triethyl amine, 30 ml of ethanol and 30 ml of tetrahydrofuran were charged into 300 ml autoclave, and the resulting mixture was maintained therein at 30° to 40° C. under hydrogen pressure of 2 kg/cm$^2$G and reacted for 24 hours.

The optical rotation, $[\alpha]_D^{27}$, of N-benzoyl-phenylalanine thus formed was +32.2° C. (C$_1$, methanol). Further, the yield of amino acid obtained was 92% Th. (Theoretical yield) and the optical purity thereof was about 80%.

APPLICATION EXAMPLE 2

0.1 g of the complex obtained in Example 2, 1 g of benzamidocinnamic acid, 0.4 ml of triethyl amine, 20 ml of ethanol and 20 ml of tetrahydrofuran were charged in 300 ml autoclave, and the resulting mixture was maintained at about 30° C. under hydrogen pressure of 2 kg/cm$^2$G and reacted for 24 hours. The yield of N-benzoyl-phenylalanine was 88%. Th. and the optical purity was about 79%.

APPLICATION EXAMPLE 3

0.14 g of the complex obtained in Example 4 and 3 g of cyclohexenedicarboxylic anhydride were charged in 300 ml autoclave and the reaction was conducted at a temperature of 120° C. fo 8 hours under hydrogen pressure of 10 kg/cm$^2$G to obtain 1.1 g of the corresponding optically active lactone (1S, 2R). The optical rotation, $[\alpha]_D^{25}$, of the product was +11.71° and the yield was about 40% Th.

APPLICATION EXAMPLE 4

0.14 g of the complex obtained in Example 4, 3 g of cyclohexendicarboxylic anhydride were charged in 300 ml autoclave and the resulting mixture was maintained at a temperature of 110° C. under hydrogen pressure of 10 kg/cm$^2$G and reacted for 20 hours to obtain the corresponding lactone in a yield of 52% Th.

The ruthenium-phosphine complex catalyst according to the present invention can be used in an asymmetric hydrogenation reaction, an asymmetric reduction reaction, an asymmetric dehydrogenation reaction and the like, is prepared inexpensively as compared to the conventional rhodium-based catalysts, and is an industrial catalyst which contributes reduction of the product costs.

While the invention has been described in detail and with reference to specific embodiments thereof, it will be apparent to one skilled in the art that various changes and modifications can be made therein without departing from the spirit and scope thereof.

What is claimed is:

1. A ruthenium-phosphine complex represented by the formula (I)

$$Ru_xH_yCl_z(R\text{—}BINAP)_2(S)_p \qquad (I)$$

wherein R—BINAP represents tertiary phosphine represented by the formula (II)

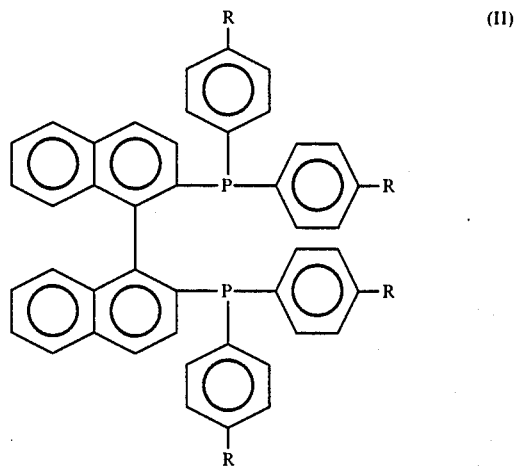

R which is the same represents hydrogen, methyl or t-butyl, S represents a tertiary amine selected from the group consisting of triethylamine, tri-n-butylamine, tri-n-octylamine, N-methyl piperidine, N-methyl pyrrolidine, N-methyl morpholine, pyridine, dimethyl aniline and tetramethyl ethylenediamine, y represents 0 or 1, and when y is 0, x represents 2, z represents 4 and p represents 1, and when y is 1, x represents 1, z represents 1 and p represents 0.

* * * * *